United States Patent [19]

Calvo et al.

[11] Patent Number: 5,403,594
[45] Date of Patent: Apr. 4, 1995

[54] ORAL SPIRAMYCIN FORMULATIONS AND METHOD FOR PREPARING SAME

[75] Inventors: Ana Calvo, Madrid; Luis A. Del Rio, Magadahonda Madrid; Manuel Esteban, Almeria, all of Spain; Robert Rona, Saint Germain en Laye, France

[73] Assignee: Rhone-Poulenc Rorer S.A., Antony Cedex, France

[21] Appl. No.: 66,068

[22] PCT Filed: Nov. 22, 1991

[86] PCT No.: PCT/FR91/00927
§ 371 Date: Jul. 16, 1993
§ 102(e) Date: Jul. 16, 1993

[87] PCT Pub. No.: WO92/09269
PCT Pub. Date: Jun. 11, 1992

[30] Foreign Application Priority Data

Nov. 26, 1990 [FR] France .................... 90 14726

[51] Int. Cl.⁶ .................... A61K 9/16; A61K 9/50; A61K 31/70
[52] U.S. Cl. .................... 424/489; 428/402.24; 514/777; 514/937; 514/951; 514/975; 264/4.1
[58] Field of Search .................... 424/489; 264/4.1, 4.7, 264/4.33; 428/402.2, 402.21, 402.22, 402.24

[56] References Cited

FOREIGN PATENT DOCUMENTS 1413186 11/1975 United Kingdom .

OTHER PUBLICATIONS

Derwent Publications Ltd., Abstract, Accession No. 87–066792, Jan. 1987.

*Primary Examiner*—Thurman K. Page
*Assistant Examiner*—James M. Spear
*Attorney, Agent, or Firm*—Ross J. Oehler; Martin F. Savitzky; Raymond S. Parker, III

[57] ABSTRACT

Formulations of spiramycin granules may be conducted by preparing a solution of albumin in the presence of an antifoaming agent, separately preparing a suspension of spiramycin in the presence of an antifoaming agent, granulating and drying a mixture of one or more sugars and water, mixing the albumin solution and spiramycin suspension with heating to coagulate the albumin, evaporating the solvents to obtain spiramycin granules, and mixing the sugar granules and spiramycin granules. Oral spiramycin formulations prepared according to this method are also disclosed.

10 Claims, No Drawings

ORAL SPIRAMYCIN FORMULATIONS AND METHOD FOR PREPARING SAME

The present invention relates to a new method for preparing microencapsulated spiramycin granules as well as to the formulations obtained from these granules.

Spiramycin, as well as its salts and its esters, is an antibiotic with a broad activity spectrum whose use by the oral route especially in children is limited because of problems of taste. Indeed, spiramycin, its salts or its esters, has physical or chemical properties which cause, at the level of the taste buds, a bitterness which results in a problem of ingestion which may lead to the rejection of the medicinal product by vomiting phenomena.

In adults, it has been possible to circumvent these disadvantages by administering spiramycin in the form of a tablet coated with a polymer or a glaze which avoids all contact between the active ingredient and the taste buds. In young children, this solution cannot be envisaged. The pharmaceutical industry has long been searching for a liquid form which can be administered to children or to adults, which permits a correct masking of the bitterness of the active ingredient even in solution.

The preparation of microcapsules of spiramycin coated with a protein, the latter being preferably albumin, is known via the Spanish Certificate of Importation No. 550171/7. It is specified in this text that the microcapsules can be used for the preparation of liquid suspensions. The method for preparing the said microcapsules is not easy to implement, it consists in preparing a mixture of spiramycin and albumin, in coagulating the albumin with heat, then in washing the solid obtained several times, in centrifuging it and then in drying it. It is specified in the text that the microcapsules have an irregular shape.

The present invention has made it possible to prepare ready-for-use granules composed of spiramycin encapsulated in albumin and diluted with a mixture of sugars and aromatic substances. The mode of preparation is greatly facilitated compared with the method described in the Spanish certificate mentioned above. Indeed, it no longer requires intermediate stages for washing the microcapsules in order to remove the solvent and makes it possible, in addition, to carry out all the stages in the same apparatus until the final formulation is obtained.

This method for preparing ready-for-use spiramycin formulations consists:
- in a first stage, in preparing a solution of albumin in a phosphate buffer at pH 7.5 to 8.5 in the presence of an antifoaming agent;
- in a second stage, in preparing a suspension of spiramycin in isooctane in the presence of an antifoaming agent;
- in a third stage, in preparing a mixture containing sugars and water, in granulating it and drying it by stirring under vacuum;
- in a fourth stage, in mixing, in a turbosphere, the solution and suspension of stages 1 and 2 based on an albumin over spiramycin weight ratio of between 0.3 and 0.5, in heating the mixture to a temperature of between 35° and 40° C. in order to emulsify it, and then in heating it to a higher temperature in order to coagulate the albumin;
- in a fifth stage, in evaporating, under vacuum, the solvents of the preceding mixture at a temperature of less than 65° C., under a pressure of less than 100 torrs;
- in a sixth stage, in mixing the granules obtained in the third stage and in the fifth stage, based on a weight ratio of between five to one and fifty to one, optionally adding aromatic substances, sweeteners and/or colourings.

According to one embodiment of the invention, during the first stage, an aqueous solution, buffered to pH 7.5–8.5 by mixing disodium and monopotassium phosphate, is prepared in particular. The antifoaming agent which is added to this solution may be of chemical or physical origin. The physical agent may be a vacuum, the chemical agent may be chosen from anionic, cationic or nonionic surface-active agents (fatty acid esters and/or ethers). The use of sorbitan oleate is preferred. According to a preferred embodiment of the invention, about 0.3% by weight of sorbitan trioleate is added as antifoaming agent to the buffered aqueous solution and finally albumin is added based on a weight ratio relative to the buffered aqueous solution of about 20%. The stirring is maintained for a few hours until the albumin dissolves completely.

According to an improved embodiment of the invention, the pH is preferably adjusted to between 7.9 and 8.1 and the temperature is maintained between 25° and 35° C.

According to one embodiment of the second stage of the invention, the spiramycin is dispersed in the turbosphere in a mixture of isooctane and antifoaming agent, preferably containing about 3.5% by weight of sorbitan trioleate relative to the isooctane, the weight ratio between the spiramycin and the isooctane/sorbitan trioleate mixture being between 50 and 100%. According to an improved embodiment of the invention, the use of a weight ratio of 80% is preferred.

According to one embodiment of the third stage of the invention which may equally well be a first stage or a fifth stage of the method according to the invention or not exist if the sugar granule is available, a granule of sugars, for example a mixture of lactose and fructose and water is prepared, granulated and dried. This granulation may be carried out in the turbosphere or in any other mixer/dryer, preferably before encapsulation of the spiramycin so as not to have to empty the turbosphere during manufacture. This granule is preferably screened in order to retain a particle size of less than 0.4 mm.

According to one embodiment of the fourth stage of the invention, the solution of albumin in the buffer is introduced into the turbosphere containing the spiramycin dispersed in isooctane. A quantity of albumin solution is preferably introduced such that the weight ratio of albumin to spiramycin is between 0.3 and 0.5. This introduction is carried out most preferably by increasing the turbosphere stirring speed to the region of 70 to 90 revolutions per minute, the temperature being fixed especially between 35° and 45° C. This stirring makes it possible to obtain a stable emulsion. To avoid destroying the protein during coagulation, the stirring is advantageously reduced to 10 to 30 revolutions per minute while maintaining the temperature below 65° C.

According to the fifth stage of the method of the invention, the solvents of the preceding mixture, that is to say water and isooctane, are evaporated under vacuum at a temperature of between 50° and 65° C. The stirring is slowed down, preferably to about 5 to 10 revolutions per minute and the vacuum is applied slowly up to a value of less than 100 torrs and preferably up to a value of between 10 and 40 torrs, the temperature being, for its part, preferably maintained below 60° C. The encapsulated spiramycin obtained is screened so as to retain only the particle size below 0.3 mm.

According to the sixth stage of the method according to the invention, the microcapsule granules obtained in the preceding stage are mixed with the granules, consisting of sugar, obtained in the third stage or in another stage of the method, and the aromatic substances, the sweeteners and the colourings are added. According to a preferred mixture, the sugar granules are added to the granules of microencapsulated spiramycin based on a weight ratio of five to one to fifty to one.

The oral formulations, based on spiramycin encapsulated with albumin, which can be used and which are obtained by the method of the invention, preferably contain doses of between 150,000 to 3,000,000 international units of spiramycin, and still more preferably, they contain 250,000 international units of spiramycin per gram of mixture. They are tasteless and can therefore be easily ingested both by children and by adults.

The present invention will be more completely described with the aid of the following example which should not be considered as limiting the invention.

EXAMPLE a) Preparation of the Buffer 107.17 kg of demineralised water (which corresponds to an excess of 40% of [sic] to subsequent losses), 0.938 kg of anhydrous disodium sodium phosphate and 0,053 kg of monopotassium phosphate are mixed. After stirring for five minutes, a sample is taken in order to measure the pH which must be in the range 7.9–8.1. If the pH is too high, potassium phosphate is added, if it is too low, sodium phosphate is added.

b) Addition of Albumin

There are added into the preceding solution 0.407 kg of sorbitan trioleate as antifoam and 27.04 kg of egg albumin, avoiding the formation of lumps. The mixture is stirred for three hours until total dissolution is obtained. At the end of this time, the mixture is filtered on a 0.2-mm filter in order to remove the foam formed.

c) Encapsulation

A Moritz TSI—500 Pharma turbosphere, heated by means of the jacket to a temperature of 40° C., is used. 44,572 kg of spiramycin are added followed by a charge of 75 liters of isooctane. The paddles of the turbosphere are set into operation at a speed of 20 revolutions per minute. 1,937 kg of sorbitan trioleate are then charged, dissolved in 6.84 liters of isooctane. The suspension is homogenised at 40 revolutions per minute for 10 minutes.

The stirring speed is increased to 70–90 revolutions per minute and 96.863 kg of the albumin solution are added thereto. The duration of the addition is 10 to 20 minutes and the temperature of the solution is 35° to 42° C. The emulsion is then homogenised for another 5 to 10 minutes. The stirring is stopped and the appearance of a stable emulsion with a yellow-white colour is observed.

To coagulate the albumin, the temperature of the jacket is increased up to 80°-85° C. and the stirring speed is again increased up to 20 to 30 revolutions per minute. When the first coagulation of the mass begins at around 50°-53° C., the stirring is reduced to 15–20 revolutions per minute in order to avoid too much extrusion of isooctane from the mass. As the coagulation of the albumin progresses towards 56°-59° C., the stirring is again reduced down to 10–15 revolutions per minute in order to avoid as much as possible the extrusion of isooctane from the microcapsules. When the whole has become coagulated at around 61° C. the temperature of the jacket is reduced so as to modify the temperature of the medium as slowly as possible.

d) Drying

When the temperature of the medium reaches 65° C. the vacuum is applied and the stirring is reduced to 5 to 10 revolutions per minute. The heating is reduced slowly, taking care to ensure that the inner temperature does not exceed 65° C. The speed of application of the vacuum is established as slowly as possible and the rate of evaporation of the mass which is most easily controlled corresponds to an inner temperature of 50° C. At this moment, the vacuum can be increased to under 100 torrs and even up to 10 to 40 torrs. When the product is sufficiently dry, it is discharged and it is screened on a 0.3-mm screen.

e) Basic Granules 66.822 kg of lactose and 100.233 kg of fructose are introduced into the turbosphere after screening on a 0.4-mm screen. The stirring is carried out at 20 revolutions per minute for 30 minutes. 2.406 liters of water are added and the mixture is kneaded. The turbosphere is heated to 70°-75° C. and the vacuum is applied. Within two to four hours, a granule having a diameter of less than 0.4 mm is obtained.

f) Final Mixture 0.134 kg of colouring, 16.706 kg of microencapsulated spiramycin (25% of the production), 3.341 kg of powdered raspberry flavouring, 3.341 kg of banana flavouring and 2,673 kg of aspartame are added to the sugar granules previously prepared. After 45 to 60 minutes, complete homogeneity is obtained. The powder obtained is passed over a screen with a mesh size of less than 0.4 mm and distributed into suitable packagings.

We claim:

1. A method for preparing formulations of spiramycin granules comprising the steps of:
   in a first stage, preparing a solution of albumin in a phosphate buffer at pH 7.5 to 8.5 in the presence of an antifoaming agent;
   in a second stage, preparing a suspension of spiramycin in isooctane in the presence of an antifoaming agent;
   in a third stage, preparing a mixture containing one or more sugars and water and granulating and drying by stirring under vacuum;
   in a fourth stage, mixing the solution of the first stage and the suspension of the second stage in a turbosphere based on an albumin over spiramycin weight ratio of between 0.3 and 0.5 and heating the mixture to a temperature of between 35° C. and 40° C. in order to emulsify it and heating the mixture to a higher temperature in order to coagulate the albumin;
   in a fifth stage, evaporating the solvents of the preceding mixture at a temperature of between 50° C. and 65° C. under pressure of less than 100 Torr to obtain spiramycin granules;

and in a sixth stage, mixing the granules obtained in the third stage and in the fifth stage based on a weight ratio of between 5:1 and 50:1.

2. Method according to claim 1, wherein the antifoaming agent is either a vacuum or a surface-active agent.

3. Method according to claim 1, wherein in the first stage, a solution of albumin containing about 20% by weight of albumin and about 0.3% by weight of sorbitan oleate is prepared.

4. Method according to claim 1, wherein in the second stage, a suspension containing 50 to 100 g of spiramycin per 100 g of isooctane and about 0.3% of sorbitan oleate is prepared.

5. Method according to claim 1, wherein in the third stage, granules having a particle size of less than 0.4 mm are prepared.

6. Method according to claim 1, wherein in the fourth stage, during the coagulation of the albumin, the emulsion is heated to a temperature of less than 65° C.

7. Method according to claim 1, wherein in the fifth stage, the solvents are evaporated under a pressure of between 10 and 40 torrs.

8. A method according to claim 1, further comprising, following the fifth stage, removing granules having a particle size of more than 0.3 mm.

9. An oral pharmaceutical composition comprising a spiramycin compound, encapsulated in albumin prepared according to the method of claim 1.

10. The oral pharmaceutical formulation of claim 9 further comprising sugar, aromatic substances and a sweetener and wherein the formulation contains a dose of 25,000 international units of spiramycin per gram of mixture.

* * * * *